US00PP28317P3

(12) United States Plant Patent
Ranney

(10) Patent No.: US PP28,317 P3
(45) Date of Patent: Aug. 22, 2017

(54) ***HYDRANGEA ARBORESCENS* PLANT NAMED 'NCHA3'**

(50) Latin Name: *Hydrangea arborescens*
Varietal Denomination: NCHA3

(71) Applicant: Thomas Green Ranney, Arden, NC (US)

(72) Inventor: Thomas Green Ranney, Arden, NC (US)

(73) Assignee: North Carolina University, Raleigh, NC (US)

( * ) Notice: Subject to any disclaimer, the term of this patent is extended or adjusted under 35 U.S.C. 154(b) by 39 days.

(21) Appl. No.: 14/545,795

(22) Filed: Jun. 18, 2015

(65) Prior Publication Data

US 2016/0374245 P1 Dec. 22, 2016

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Keith Robinson
(74) *Attorney, Agent, or Firm* — Cassandra Bright

(57) ABSTRACT

A new and distinct *Hydrangea* cultivar named 'NCHA3' is disclosed, characterized by large, mop-head inflorescences with prevalent sterile flowers. Flower buds are red and open with dark pink sepals. Plant habit is compact, and plants are triploid. The new variety is a *Hydrangea* normally produced as an outdoor garden or container plant.

4 Drawing Sheets

Latin name of the genus and species: The Latin name of the novel plant variety disclosed herein is *Hydrangea arborescens*.

Variety denomination: The seedling of *Hydrangea arborescens* disclosed herein has been given the varietal denomination 'NCHA3'.

BACKGROUND OF THE INVENTION

The present invention comprises a new and distinct *hydrangea* cultivar hereinafter referred to by the cultivar name 'NCHA3'. This new *hydrangea* was developed through a breeding program at North Carolina State University, Mills River, N.C. 'NCHA3' was selected from a population of seedlings that resulted from a cross of the pollen parent *Hydrangea arborescens* H2009-068-007 (unpatented) and the seed parent *Hydrangea arborescens* H2008-143-001 (unpatented). See FIG. 1 for complete pedigree. The first asexual propagation of 'NCHA3' was carried out in July 2012 by rooting stem cuttings at the North Carolina State University, Mountain Horticultural Crops Research Station, Mills River, N.C. and has been asexually reproduced repeatedly by vegetative cuttings over a three year period. 'NCHA3' roots readily from softwood cuttings treated with a basal dip of 2,500-5,000 ppm indole butyric acid (potassium salt) in water. 'NCHA3' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Large mop-head inflorescences (i.e., a hortensia flower form) with prevalent sterile flowers.
2. Red flower buds that open with dark pink sepals.
3. Triploid cytotype.
4. Compact form.

COMPARISON WITH PARENT VARIETIES

'NCHA3' is similar to the seed parent in most horticultural characteristics, however, the new variety differs in the following:

1. The new variety has a much darker red-purple sterile sepal color.
2. The new variety has as different genome size, 3.8 pg, compared to 5.2 pg of the seed parent.

'NCHA3' is similar to the pollen parent in most horticultural characteristics, however, the new variety differs in the following:

1. The new variety has a darker red-purple sterile sepal color.
2. The new variety has as different genome size, 3.8 pg, compared to 2.7 pg of the pollen parent.

COMPARISON WITH COMMERCIAL CULTIVARS

Table 1 shows distinguishing characteristics between 'NCHA3' and other commercially available cultivars of *H. arborescens*. *Hydrangea arborescens* 'HCHA3' has a unique combination of traits including a mophead inflorescence, red flower buds that open with dark pink sepals, a very compact form, and a triploid cytotype.

TABLE 1

Comparison to other cultivars.

| Trait | Taxa: *H. arborescens* 'NCHA1' (U.S. Plant Pat. No. 20,765) | *H. arborescens* 'NCHA2' (U.S. Application No. 14/545,787) | *H. arborescens* 'NCHA3' (U.S. Application No. 14/545,795) |
|---|---|---|---|
| Ploidy level (genome size, pg) | Diploid (2.7 pg) | Triploid (3.9 pg) | Triploid (3.8 pg) |
| Growth habit | Rounded | Rounded | Rounded |
| Height and width | 100 cm × 100 cm | 80 cm × 80 cm | 60 cm × 60 cm |
| Stem internode length | 5 to 15 cm | Avg. 7 cm (typical range: 3 to 10 cm) | Avg. 6 cm (typical range: 3 to 8 cm) |
| Flowers per inflorescence | | | |
| Fertile | Approx. 600 | Approx. 150 | Approx. 150 |
| Sterile | Approx. 600 | Approx. 300 | Approx. 300 |
| Corymb diameter | 8-20 cm | Avg. 14 cm | Avg. 12 cm |
| Sepal color | | | |
| Above | Red-Purple (ranges from 68D/C to N66D/N66C) | Red-Purple (65A to 67C) fading to Red-Purple (65C) | Red-Purple (60C) fading to Red-Purple (70C) |
| Below | Red-Purple (ranges from 68D/C to N66D/N66C) | Red-Purple (63B) | Red-Purple (60A) |
| Sepal | | | |
| Length | 0.5-0.7 cm | Avg: 1.2 cm | Avg. 1.0 cm |
| Width | 0.3-0.5 cm | Avg. 1.0 cm | Avg. 0.7 cm |

| Trait | Taxa: *H. arborescens* 'NCHA4' (U.S. Application No. 14/545,796) | *H. arborescens* 'PIIHA-I' (U.S. Plant Pat. No. 21,227) |
|---|---|---|
| Ploidy level (genome size, pg) | Triploid (3.8 pg) | Unknown |
| Growth habit | Rounded | Upright, spreading |
| Height and width | 80 cm × 80 cm | 90 cm × 90 cm |
| Stem internode length | Avg. 7 cm (typical range: 3 to 10 cm) | About 6 cm |
| Flowers per inflorescence | | |
| Fertile | Approx. 200 | Approx. 75 |
| Sterile | Approx. 400 | Approx. 300 |
| Corymb diameter | Avg. 20 cm | Avg. 12.5 cm |
| Sepal color | | |
| Above | Red-Purple (63D to 65B) | Close to Red-Purple (58A) |
| Below | Red-Purple (63A) | Close to Red-Purple (63A) |
| Sepal | | |
| Length | Avg. 1.0 cm | 0.7 cm |
| Width | Avg. 0.7 cm | 0.5 cm |

BRIEF DESCRIPTION OF THE DRAWINGS

This new *hydrangea* is illustrated by the accompanying photographs which show the plant's pedigree, form, foliage and inflorescences. Photographs were taken on 2-year-old plants. The colors shown are as true as can be reasonably obtained by conventional photographic procedures. Colors in the photographs may differ slightly from the color values cited in the detailed botanical description, which accurately describe the colors of the new *hydrangea*.

DETAILED BOTANICAL DESCRIPTION

The following is a detailed description of the botanical characteristics of the new and distinct *hydrangea* variety plant known by the denomination 'NCHA3'. The detailed description was taken on a three-year-old field-grown plant in Mills River, N.C. in 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Hydrangea arborescens* 'NCHA3'.

*Common name.*—Smooth *Hydrangea.*

Figure 1:
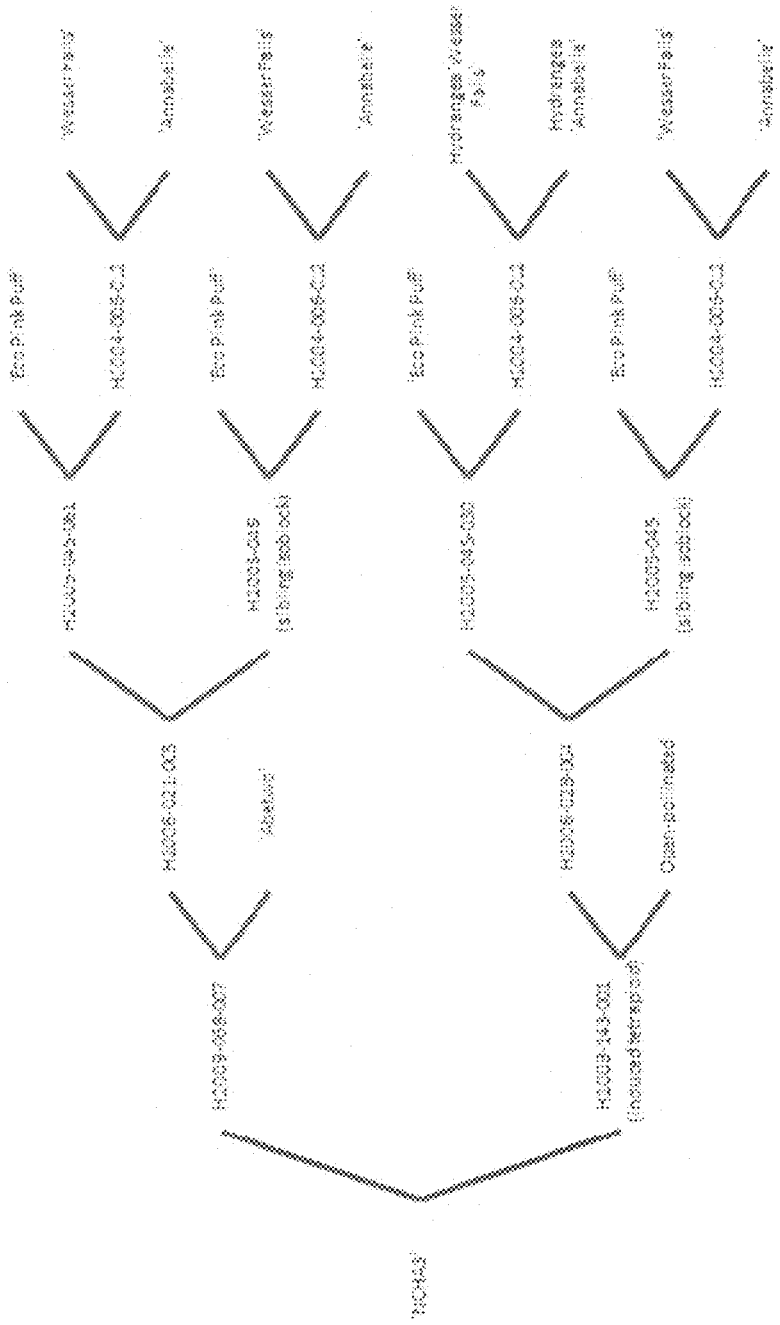
FIG. 1 Shows the pedigree of 'NCHA3'.
Figure 2:
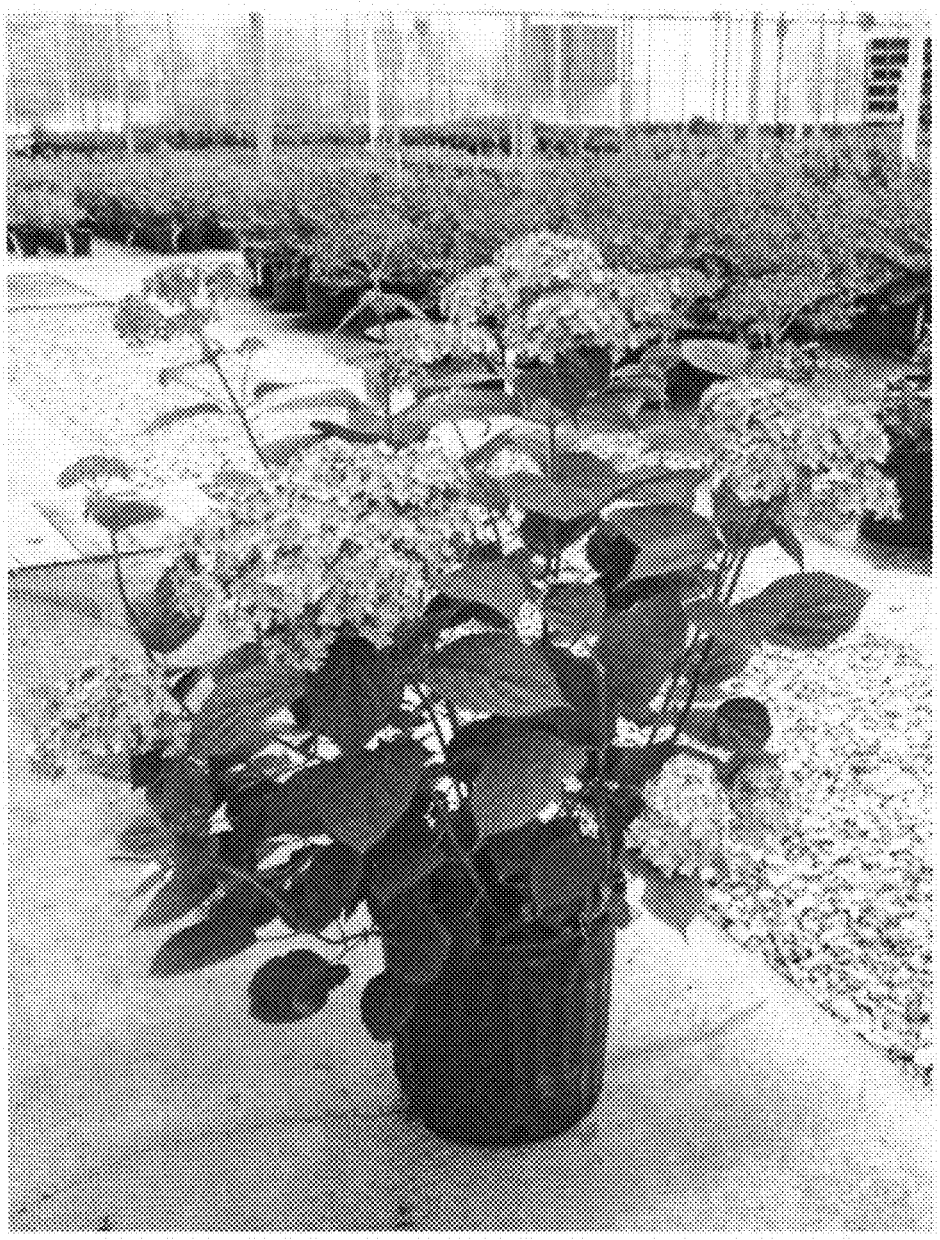
FIG. 2 Shows the form of a container-grown plant in flower.
Figure 3:
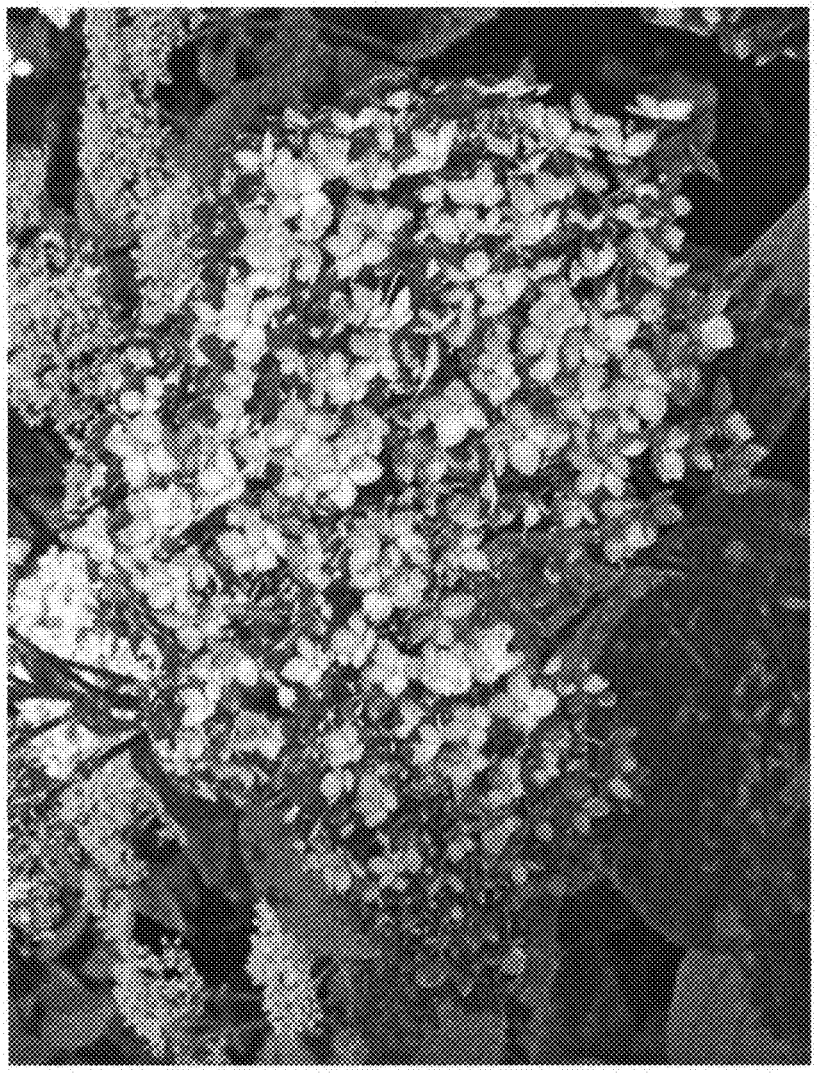
FIG. 3 Shows the form of a field-grown plant in flower.
Figure 4:
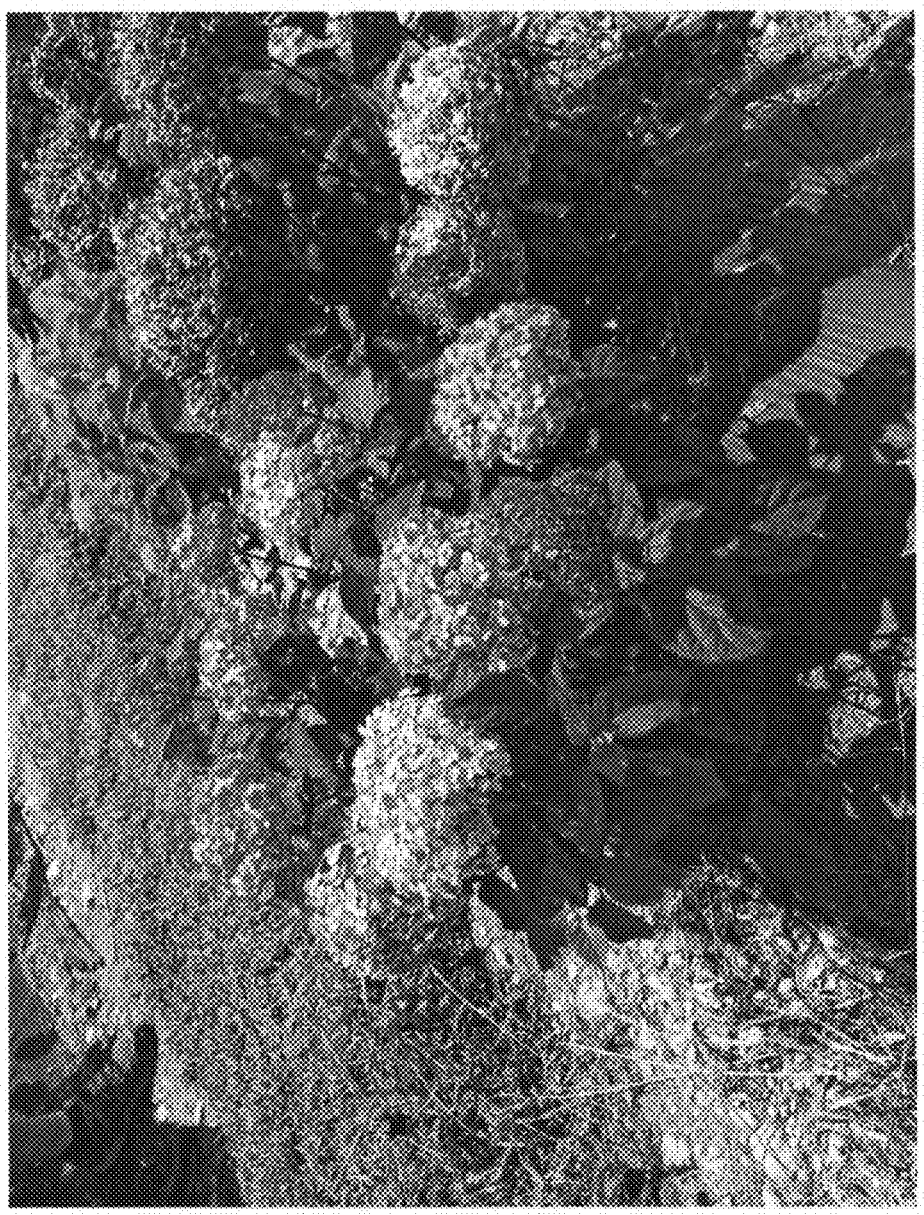
FIG. 4 Shows the deep pink mop-head inflorescence.

Parentage: 'NCHA3' originated as a seedling that resulted from a cross of *H. arborescens* H2009-068-007 and *H. arborescens* H2008-143-001. See FIG. 1 for extended pedigree.

Plant description:

*Growth habit.*—Rounded. Non-climbing.

*Height* (*from top of soil including inflorescences*).—About 60 cm.

*Width* (*including inflorescences*).—About 60 cm.

Shoot and stem:

*Shoot length.*—50 cm (typical range: 40 to 60 cm).

*Shoot diameter.*—0.5 cm (typical range: 0.3 to 0.9 cm).

*Internode length.*—6 cm (typical range: 3 to 8 cm).

*Shoot texture* (*current year*).—Pubescent.

*Shoot color* (*current year*).—Yellow-Green (146C).

*Mature stem texture* (*from prior year*).—Glabrous.

*Mature stem color* (*from prior year*).—Grey-Brown (199D).

*Fasciation.*—Not present.

*Lenticels.*—Not present.

Branching habit: Freely branching with 50-80 shoots.

Leaves:

*Type.*—Simple. Not lobed.

*Persistence.*—Deciduous.

*Arrangement.*—Opposite.

*Shape.*—Broadly ovate.

*Apex.*—Acuminate. Tip Approximately 4 to 7 mm.

*Base.*—Acute to rounded.

*Variegation.*—Not variegated.

*Venation.*—Pinnate, opposite to subopposite.

*Vein color*.—Upper: Yellow-Green (148B). Lower: Yellow-Green (148D).

*Margins*.—Dentate to serrate.

*Texture*.—Upper surface: Glabrous. Lower surface: Slightly pubescent.

*Emerging leaves*.—Color: Upper and lower: Yellow-Green (146B).

*Mature leaves during growing season*.—Color: Upper: Green (147A). Lower: Yellow-Green (146A to 146B). Length of lamina: Avg. 8 cm (typical range: 5 to 11 cm). Width: Avg. 6 cm (typical range: 4 to 8 cm).

*Leaf attachment*.—Petiolate.

*Petiole*.—Length: Avg. 3 cm (typical range: 1 to 4 cm). Diameter: Avg. 0.2 cm (typical range: 0.15 to 0.25 cm). Color: Brown (200C to 200D).

Inflorescence:

*Description*.—Fertile (approximately 300) and sterile (approximately 150) flowers arranged on individual hemispherical or dome-shaped terminal, compound corymbs. Fertile flowers moderately conspicuous.

*Flowering season*.—Late May to late June in Mills River, N.C.

*Corymb*.—Diameter: Average 12 cm (typical range: 7 to 14 cm). Height: Average 7 cm (typical range: 5 to 8 cm). Quantity: Often 50-80 corymbs per plant over the flowering season. Longevity: Showy for approximately 4 weeks.

*Sterile flowers*.—Petals, pistils and stamens are greatly reduced (<0.5 mm).

*Buds*.—Shape: Oval. Diameter: 0.2 cm. Color: Red-Purple (59B). Sepals: Number: 2 to 4. Length: Avg. 1.0 cm (typical range: 0.7 to 1.2 cm). Width: Avg. 0.7 cm (typical range: 0.5 to 1.0 cm). Shape: Oval. Apex: Mucronate to rounded. Base: Rounded. Margin: Entire. Texture: Glabrous upper and lower surfaces. Color: Upper: Red-Purple (60C) fading to Red-Purple (70C). Lower: Red-Purple (60A).

*Fertile flowers*.—Sepals and petals are greatly reduced (<0.5 mm). Buds: Shape: Round. Diameter: 0.2 cm. Color: Red-Purple (59B). Width: 0.2 cm. Height: 0.2 cm.

Reproductive organs:

*Gynoecium*.—Pistil number: 2, fused. Pistil color: White (155B). Pistil length: 0.2 cm. Stigma shape: Blunt. Stigma diameter: 0.025 cm. Style length: 0.1 cm (typical range: 0.095 to 0.109 cm). Ovary shape: Rounded. Ovary diameter: 0.1 cm. Ovary color: Near Yellow-Green 145B.

*Androecium*.—Stamen number: 10. Anther: Shape: Rounded, fusiform. Length: 0.05 cm. Color: White (158D). Filament: Length: 0.07 cm. Color: White (155B). Amount of pollen: None observed.

OTHER CHARACTERISTICS

Fruit/seed set: Seeds are minute, dust-like. Not accurately measured with R.H.S. chart.

Disease and insect resistance: No significant disease or insect pests have been observed.

Cold hardiness: At least USDA zone 6b; testing has not been completed in colder zones.

Genome size: Flow cytometry was conducted to determine DNA content which is directly correlated with ploidy among closely related taxa. Holoploid, 2C DNA content was determined on newly expanded leaf tissue. Nuclei were extracted, stained with 4',6-Diamidino-2-phenylindole (DAPI), and analyzed (minimum of 5,000 nuclei per sample) using a flow cytometer (PA-I, Partec, Münster, Germany). *Pisum sativum* L. 'Ctirad', with a known genome size of 8.75 pg was used as an internal standard. 2C DNA content for 'NCHA3' was 3.8 pg, approximately 1.5 times the DNA content of a diploid (e.g., 'NCHA1'), and consistent with being a triploid as would be expected from an interploid cross between diploid and tetraploid parents (see Table 1).

What is claimed is:

1. A new and distinct cultivar of *Hydrangea arborescens* named 'NCHA3' as illustrated and described herein.

* * * * *

Pedigree of *Hydrangea arborescens* 'NCHA3'.